(12) United States Patent
Stoffers

(10) Patent No.: US 9,018,163 B2
(45) Date of Patent: Apr. 28, 2015

(54) MODULATING PDX-1 WITH PCIF1, METHODS AND USES THEREOF

(75) Inventor: Doris Stoffers, Moorestown, NJ (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 924 days.

(21) Appl. No.: 12/440,900

(22) PCT Filed: Mar. 3, 2008

(86) PCT No.: PCT/US2008/002792
§ 371 (c)(1),
(2), (4) Date: Nov. 9, 2009

(87) PCT Pub. No.: WO2008/109034
PCT Pub. Date: Sep. 12, 2008

(65) Prior Publication Data
US 2012/0003242 A1 Jan. 5, 2012

Related U.S. Application Data

(60) Provisional application No. 60/904,364, filed on Mar. 2, 2007.

(51) Int. Cl.
C07K 16/18 (2006.01)
A01N 37/18 (2006.01)
C12N 5/00 (2006.01)
C07K 16/00 (2006.01)

(52) U.S. Cl.
CPC ..................................... *C07K 16/18* (2013.01)

(58) Field of Classification Search
USPC .......... 435/6, 91.1, 91.31, 455, 458, 7.1, 377; 514/1, 2, 44, 6.8, 6.9; 536/23.1, 24.5; 424/93.7, 172.1; 530/387.1, 388.24
See application file for complete search history.

(56) References Cited

FOREIGN PATENT DOCUMENTS

WO    WO 02/44321    *   6/2002

OTHER PUBLICATIONS

Liu, A., et al. Mol. Cell. Biol. 2004;24(10):4372-4383.*
Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Holen et al., Nucleic Acids Res., vol. 30, No. 8, pp. 1757-1766 (2002).*
Opalinska et al., Nature Rev., vol. 1, pp. 503-514 (2002).*
Nielsen et al, "Synthesis of 29-O,39-C-linked bicyclic nucleosides and bicyclic oligonucleotides", 1997 J. Chem. Soc. Perkin Trans. 1, 3423.
Koshkin et al, "Novel convenient syntheis of LNA [2.2.1]Bicyclo Nucleosides", 1998, Tetrahedron Letters 39, 4381.
Singh & Wengel "Universality of LNA-mediated high-affinity nucleic acid recognition", 1998 Chem. Commun. 1247.
Singh et al, "LNA (locked nucleic acids): synthesis and high-affinity nucleic acid recognition", 1998 Chem. Commun. 455.
Peshavaria et al., "The PDX-1 activation domain provides specific functions necessary for transcriptional stimulation in pancreatic beta-cells", Mol. Endocrinol. 2000, vol. 14, pp. 1907-1917.
Liu et al., "Identification of PCIFI, a POZ domain protein that inhibits PDX-1 (MODY4) transcriptional activity", Mol. Cell Biol. 2004, vol. 24 No. 10, pp. 4372-4383.
Liu et al., "Two conserved domains in PCIF1 mediate interaction with pancreatic transcription factor PDX-1", FEBS letter. 2006, vol. 580, pp. 6701-6706.
Wang et al., "Inhibition of insulin-like growth factor-I receptor (IGF-IR) signaling and tumor growth by a fully human neutralizing anti-IGF-IR antibody" Mol. Cancer Ther. 2005, vol. 4, No. 8, pp. 1214-1221.
Kulas et al., "Insulin receptor signaling is augmented by antisense inhibition of the protein tyrosine phosphatase LAR", J. Biol. Chem. 1995, vol. 270, No. 6, pp. 2435-2438.

* cited by examiner

*Primary Examiner* — Jane Zara
(74) *Attorney, Agent, or Firm* — Mark S. Cohen; Pearl Cohen Zedek Latzer Baratz LLP

(57) ABSTRACT

This invention relates to PCIF1 and its use as a target for the improvement of pancreatic islet β cell mass and function in diabetes. Specifically, the invention relates to the use of compounds capable of modulating the expression or function of PCIF1 and their effect on the function of Pdx-1.

3 Claims, 15 Drawing Sheets

E16.5 pancreas, PDX-1 stain

MODULATING PDX-1 WITH PCIF1, METHODS AND USES THEREOF

CROSS-REFERENCE TO RELATED APPLICATIONS

This application is a National Phase Application of PCT International Application No. PCT/US08/02792, International Filing Date Mar. 3, 2008, claiming priority of U.S. Provisional Patent Application, 60/904,364, filed Mar. 2, 2007, both which are incorporated herein by reference in their entirety.

GOVERNMENT INTEREST

This invention was supported, in part, by funding from the NIH. The government may have certain rights in the invention.

FIELD OF INVENTION

This invention is directed to PCIF1 and its use as a target for the improvement of pancreatic islet β cell mass and function in diabetes. Specifically, the invention relates to the use of compounds capable of modulating the expression or function of PCIF1 and their effect on the function of Pdx-1.

BACKGROUND OF THE INVENTION

Diabetes results from an imbalance between insulin production by the pancreatic β-cell and insulin action on metabolic tissues such as the liver, fat and muscle. In type 1 diabetes, an autoimmune attack on endogenous cells β results in nearly absolute insulin deficiency, whereas in type 2 diabetes, resistance to the action of insulin is a major component of the pathophysiology. Pancreatic β cells have remarkable ability to compensate for insulin resistance, by increasing insulin synthesis and secretion and by expanding the number of β cells. Therefore, hyperglycemia and the attendant complications of chronic hyperglycemia on the kidney, eye, and heart, causing blindness, kidney failure and heart disease, result only when β cells can no longer compensate due to genetic or environmentally induced insults. Therefore, efforts to understand the development of islet beta cell mass and to promote islet compensation for insulin resistance may lead to successful therapeutic strategies for the treatment of all forms of diabetes.

PDX-1 is a Hox type homeodomain-transcription factor that is pivotally positioned in the transcriptional hierarchy governing β cell development. PDX-1 is expressed in a biphasic manner during embryonic and fetal pancreas development and it plays two critical roles, first in the early development of both the endocrine and exocrine pancreas, and then in the later differentiation of the β cell. Deficiencies in Pdx1/IPF-1 show pancreatic agenesis, whereas heterozygous PDX-1 mutation leads to the development of an initially normal morphological mass of β cells but impaired β cell function, leading later to abnormal glucose tolerance in mice and early-(MODY4) and late-onset forms of type 2 diabetes in humans. PDX-1 is recognized as a transcriptional activator of key islet and β cell specific genes, including insulin, somatostatin, Glut2, and IAPP.

Therefore modulation of PDX-1 presents a potential therapeutic pathway target in the treatment of several pathologies associated with abnormal glucose metabolism.

SUMMARY OF THE INVENTION

In one embodiment, the invention provides a method of increasing pancreatic β-cell mass in a subject, comprising the step of contacting a cell of said subject with a composition comprising an anti-PCIF1 antibody capable of inhibiting binding of PCIF1 to PDX-1, thereby increasing pancreatic β-cell mass in a subject.

In another embodiment, the invention provides a method of increasing pancreatic β-cell mass in a subject, comprising the step of contacting a cell of the subject with a composition capable of inhibiting the expression of a nucleotide sequence encoding PCIF1, thereby increasing pancreatic β-cell mass in a subject.

In one embodiment, the invention provides a method of increasing glucagon-producing α-cell mass in a subject, comprising the step of contacting the cell with a composition comprising a nucleotide sequence capable of inhibiting the expression of a nucleotide sequence encoding PCIF1, thereby increasing glucagon-producing α-cell mass in a subject.

In another embodiment, the invention provides a method of treating glucose intolerance in a subject, comprising the step of inhibiting the expression or function of PCIF1 or an encoded protein thereof.

In one embodiment, the invention provides a method of inhibiting or suppressing glucose intolerance in a subject, comprising the step of inhibiting the expression or function of PCIF1 or an encoded protein thereof.

In another embodiment, the invention provides a method of reducing symptoms associated with glucose intolerance in a subject, comprising the step of inhibiting the expression or function of PCIF1 or an encoded protein thereof.

In one embodiment, the invention provides a method of increasing endogenous levels of PDX-1 in embryonic stem cells (ES) comprising the step of downregulating the expression of PCIF1 in the embryonic stem cells, thereby promoting of β-cell differentiation.

In another embodiment, the invention provides a method of preventing degradation of PDX-1 protein levels in adult human β cells comprising the step of downregulating the expression of PCIF1 gene, thereby decreasing β cell apoptosis, increasing replication and differentiation.

In one embodiment, the invention provides a method of reducing the number of islets needed to achieve cure in a diabetic subject treated with islet transplantation, comprising the step of transplanting in the subject islet cells comprising downregulated PCIF1 expression or function, thereby increasing β-cell mass.

In another embodiment, the invention provides a method of screening a set of compounds for a compound capable of modulating β cell mass, increasing new β cell differentiation from progenitor cells, decreasing β cell apoptosis, increasing replication of existing β cells, increasing differentiation of new α cells from progenitor cells, or their combination, comprising the steps of: contacting a β cell with a candidate compound; and analyzing the β cell for the expression of PCIF1 gene, or capability of its encoded protein to bind to PDX-1, whereby a candidate compound capable of inhibiting the expression of PCIF1 gene, or capability of its encoded protein to bind to PDX-1 is a candidate compound for increasing β cell mass, increasing new β cell differentiation from progenitor cells, decreasing β cell apoptosis, increasing replication of existing β cells, increasing differentiation of new α cells from progenitor cells, or their combination.

In one embodiment, the invention provides a method of treating congenital hyperinsulinism (CHI) in a subject, comprising the step of contacting the subject with a composition comprising a compound capable of increasing the expression of PCIF1 or its function in the subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

This invention relates in one embodiment to PCIF1 and its use as a target for the improvement of pancreatic islet β cell mass and function in diabetes. Specifically, the invention relates to the use of compounds capable of modulating the expression or function of PCIF1 and their effect on the function of Pdx-1.

In one embodiment, the invention provides a method of increasing pancreatic β-cell mass in a subject, comprising the step of contacting a cell of said subject with a composition comprising an anti-PCIF1 antibody capable of inhibiting binding of PCIF1 to PDX-1, thereby increasing pancreatic β-cell mass in a subject.

In one embodiment, pancreatic duodenal homeobox 1 (Pdx-1) is one of the earliest markers of pancreatic morphogenesis. Its expression is also maintained throughout the life of the β-cell, indicative of its crucial role in normal β-cell development and function. Pdx-1, referred to in certain other embodiments as Ipf-1, Idx-1, Stf-1, GSF, and IUF-1 is a transcription factor expressed in pancreatic islets and duodenum that transactivates the insulin and somatostatin genes. Targeted disruption of the Pdx1 gene leads in one embodiment, to the failure of pancreas formation, and in another embodiment, a homozygous inactivating Pdx1 mutation is associated with congenital pancreatic agenesis, underscoring the critical role of Pdx1 in early pancreas formation.

In insulin resistant states in one embodiment, and in hyperglycemia in another embodiment, Pdx-1 is required for compensatory β-cell proliferation and islet hyperplasia. In two different models of insulin resistance, insulin receptor/insulin receptor substrate-1 (IR/IRS-1) transheterozygous mice and liver specific insulin receptor knockout mice (LIRKO), haploinsufficiency for Pdx-1 limited β cell proliferation required for compensatory islet hyperplasia and hyperinsulinemia that is otherwise seen. In another embodiment of insulin resistance, Pdx-1 haploinsufficiency superimposed on heterozygosity for glucose transporter (Glut4+/−), while decreasing insulin levels, does not affect compensatory islet hyperplasia. The role of Pdx-1 in regulation of β-cell mass is evident in one embodiment in IRS2-null mice which have reduced Pdx-1 expression and develop diabetes at 2 months of age. In another embodiment, further reduction in Pdx-1 exacerbates diabetes, while Pdx-1 overexpression in these mice is associated with a two-fold increase in beta-cell area, islet size and beta-cell proliferation, as well as improvement in glucose tolerance. In one embodiment, contacting a cell of said subject with a composition comprising a composition capable of inhibiting expression or function PCIF1 using the methods provided herein, such as in the use of an anti-PCIF1 antibody capable of inhibiting binding of PCIF1 encoded by PCIF1 to PDX-1, results in increased insulin secretion.

Figure 11:
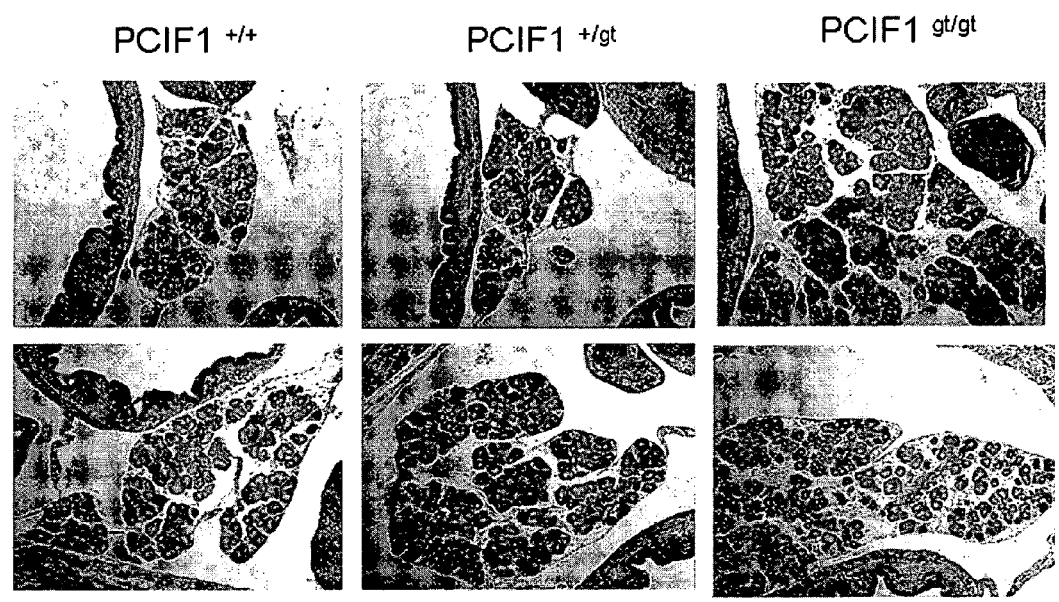
FIG. 11 shows delayed acinar differentiation in PCIF1$^{gt/gt}$ mice.

In another embodiment, increase in β-cell mass affected using the methods provided herein, is due to increased differentiation of new β cell formation from undifferentiated progenitors. In one embodiment, reduction in the expression or function of PCIF1 using the methods provided herein, delay acinar development in pancreatic cells (FIG. 11). Therefore in one embodiment, the increase in β-cell mass affected using the methods provided herein is the result of increased replication of existing β cells.

The pancreas is composed of at least three types of differentiated tissue: the hormone-producing cells in islets, the exocrine zymogen-containing acini, and the centroacinar cells, ductules and ducts (ductal tree). All of these cells appear to have a common origin during embryogenesis in the form of duct-like protodifferentiated cells. Later in life, the acinar and ductal cells retain a significant proliferative capacity that can ensure cell renewal and growth, whereas the islet cells become mitotically inactive.

The functional unit of the endocrine pancreas is the islet of Langerhans which are scattered throughout the exocrine portion of the pancreas and are composed of four cell types: alpha-, beta-, delta-, and PP-cells. Beta-cells produce insulin, represent the majority of the endocrine cells and form the core of the islets while alpha-cells secrete glucagon and are located in the periphery. Delta-cells and PP-cells are less numerous and secrete somatostatin and a pancreatic polypeptide respectively. Insulin and glucagon are key regulators of blood glucose levels. Insulin lowers blood glucose levels by increasing its cellular uptake and conversion into glycogen. Glucagon elevates blood glucose levels by intervening in the breakdown of liver glycogen. Type 1 diabetes is characterised in one embodiment, by an autoimmune destruction of insulin-producing β-cells. Type 2 diabetes is characterised by insulin resistance and impaired glucose tolerance where insulin is not efficiently used or is produced in insufficient amounts by the β-cells.

In one embodiment, the term "progenitor cell" refers to any somatic cell which has the capacity to generate fully differentiated, functional progeny by differentiation and proliferation. In another embodiment, progenitor cells include progenitors from any tissue or organ system, including, but not limited to, blood, nerve, muscle, skin, gut, bone, kidney, liver, pancreas, thymus, and the like. Progenitor cells are distinguished from "differentiated cells," which are defined as those cells which may or may not have the capacity to proliferate, i.e., self-replicate, but which are unable to undergo further differentiation to a different cell type under normal physiological conditions. Moreover, progenitor cells are further distinguished from abnormal cells such as cancer cells, especially leukemia cells, which proliferate (self-replicate) but which generally do not further differentiate, despite appearing to be immature or undifferentiated.

Progenitor cells include in another embodiment, all the cells in a lineage of differentiation and proliferation prior to the most differentiated or the fully mature cell. Thus, in one embodiment, progenitors include the β-cell progenitor in the mature individual, which is capable of differentiation to only one type of cell, but which is itself not fully mature or fully differentiated. Production of mature, functional β-cells results from proliferation and differentiation of "unipotential progenitors," i.e., those progenitors which have the capacity to make only one type of cell. In one embodiment, insulin-producing β cells are derive from pancreatic endocrine progenitors expressing the transcription factor neurogenin 3 (NGN3; also known as Atoh5 and Relax).

In one embodiment, an uncommitted progenitor cell such as embryonic stem cell, is described as being "totipotent," i.e., both necessary and sufficient for generating all types of mature cells. Progenitor cells which retain a capacity to generate all pancreatic cell lineages but which can not self-renew are termed "pluripotent." In another embodiment, cells which can produce some but not all pancreatic lineages and can not self-renew are termed "multipotent".

In one embodiment, the term "antibody" includes complete antibodies (e.g., bivalent IgG, pentavalent IgM) or fragments of antibodies which contain an antigen binding site in other embodiments. Such fragments include in one embodiment Fab, F(ab')$_2$, Fv and single chain Fv (scFv) fragments. In one embodiment, such fragments may or may not include antibody constant domains. In another embodiment, Fab's lack constant domains which are required for Complement fixation. ScFvs are composed of an antibody variable light chain ($V_L$) linked to a variable heavy chain ($V_H$) by a flexible hinge. ScFvs are able to bind antigen and can be rapidly produced in bacteria or other systems. The invention includes antibodies and antibody fragments which are produced in bacteria and in mammalian cell culture. An antibody obtained from a bacteriophage library can be a complete antibody or an antibody fragment. In one embodiment, the domains present in such a library are heavy chain variable domains ($V_H$) and light chain variable domains ($V_L$) which together comprise Fv or scFv, with the addition, in another embodiment, of a heavy chain constant domain ($C_{H1}$) and a light chain constant domain ($C_L$). The four domains (i.e., $V_H$–$C_{H1}$ and $V_L$–$C_L$) comprise an Fab. Complete antibodies are obtained in one embodiment, from such a library by replacing missing constant domains once a desired $V_H$–$V_L$ combination has been identified.

Antibodies of the invention can be monoclonal antibodies (mAb) in one embodiment, or polyclonal antibodies in another embodiment. Antibodies of the invention which are useful in the compositions, methods and kits of the invention can be from any source, and in addition may be chimeric. In one embodiment, sources of antibodies can be from a mouse, or a rat, a plant, or a human in other embodiments. Antibodies of the invention which are useful for the compositions, and methods of the invention have reduced antigenicity in humans (to reduce or eliminate the risk of formation of anti-human antibodies), and in another embodiment, are not antigenic in humans. Chimeric antibodies for use the invention contain in one embodiment, human amino acid sequences and include humanized antibodies which are non-human antibodies substituted with sequences of human origin to reduce or eliminate immunogenicity, but which retain the antigen binding characteristics of the non-human antibody.

In one embodiment, Pdx-1, in addition to its role in controlling proliferation, has been implicated in regulation of β-cell survival. Islets from Pdx-1 haploinsufficient mice show in another embodiment, increased markers of apoptosis and a 50% reduction in β-cell mass at 6 to 12 months of age. Therefore and in one embodiment, increase in β-cell mass affected using the methods provided herein is due to decreased apoptosis of existing β cells.

In one embodiment, PDX-1 and cullin-3 compete in their interactions with the PCIF1 POZ domain and in another embodiment participate together in a complex. In another embodiment, over-expression of PCIF1 and cullin-3 promotes Pdx1 degradation by proteasome. In another embodiment, in the setting of PCIF1/cullin-3 over-expression reduction of Pdx-1 is attenuated by co-administration of MG132, an established proteasome inhibitor.

In one embodiment, PCTF1 is a novel regulatory molecule that interacts with the homeodomain transcription factor PDX-1. In another embodiment, the PDX-1 C-terminus is an evolutionarily conserved region that mediates both physical and functional interaction with PCIF1. In one embodiment a human diabetes causing mutation, E224K, located within this conserved motif disrupts the functional interaction with PCTF1, indicating that interaction between PDX-1 and PCIF1 is required in another embodiment, for normal glucose homeostasis. In another embodiment, POZ domain interaction with residues in the PDX-1 C-terminus outside the conserved motif indicates that these mutations could also modify the interactions with PCIF1.

In one embodiment, both POZ and TRAF domains of PCIF1 mediate the physical interaction with PDX-1. In another embodiment inhibiting the interaction between PCIF1 and PDX-1, increases the concentration of PDX-1 in pancreatic β-cell, resulting in another embodiment, in an increase in β-cell mass. Accordingly and in one embodiment, provided herein is a method of increasing pancreatic β-cell mass in a subject, comprising the step of contacting a cell of said subject with a composition comprising an anti-PCIF1 antibody capable of inhibiting binding of PCIF1 to PDX-1, thereby increasing pancreatic β-cell mass in a subject.

In another embodiment, increasing mass or number of β-cells using the methods provided herein, is done ex-vivo, or in vivo in another embodiment.

In one embodiment, the invention provides a method of increasing pancreatic β-cell mass in a subject, comprising the step of contacting a cell of the subject with a composition capable of inhibiting the expression of a nucleotide sequence encoding PCIF1, thereby increasing pancreatic β-cell mass in a subject. In one embodiment, the composition used in the methods provided herein, which is capable of inhibiting the expression of a nucleotide sequence encoding PCIF1, comprises an agent that is a siRNA, a polyamide, a triple-helix-forming agent, an antisense RNA, a synthetic peptide nucleic acids (PNAs), an agRNA, a LNA/DNA copolymer, a small molecule chemical compound, or a combination thereof.

In one embodiment, the agent used in the compositions described herein, which are utilized in the methods provided herein, is a siRNA. In another embodiment, the agent capable of inhibiting the expression of PCIF1 is a polyamide. In another embodiment, the agent capable of inhibiting the expression of PCIF1 is a triple-helix-forming agent. In another embodiment, the agent capable of inhibiting the expression of PCIF1 is an antisense RNA. In another embodiment, the agent capable of inhibiting the expression of PCIF1 is a synthetic peptide nucleic acids (PNAs). In another embodiment, the agent capable of inhibiting the expression of PCIF1 is an agRNA. In another embodiment, the agent capable of inhibiting the expression of PCIF1 is a LNA/DNA copolymer. In another embodiment, the agent capable of inhibiting the expression of PCIF1 is a small molecule chemical compounds, or a combination thereof in another embodiment.

In one embodiment, the term "siRNA" refers to RNA interference, which in another embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved in one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response. In one embodiment, the siRNA used in the compositions and method provided herein interferes with the expression of PCIF1, thereby increasing β-cell mass.

In one embodiment, the term "conserved", refers to amino acid sequences comprising the peptides or nucleotides described herein, which remain in one embodiment, essentially unchanged throughout evolution, and exhibit homology among various species producing the protein.

In one embodiment, the terms "homology", "homologue" or "homologous", indicate that the sequence referred to, whether an amino acid sequence, or a nucleic acid sequence, exhibits, in one embodiment at least 70% correspondence with the indicated sequence. In another embodiment, the amino acid sequence or nucleic acid sequence exhibits at least 72% correspondence with the indicated sequence. In another embodiment, the amino acid sequence or nucleic acid sequence exhibits at least 75% correspondence with the indicated sequence. In another embodiment, the amino acid sequence or nucleic acid sequence exhibits at least 80% correspondence with the indicated sequence. In another embodiment, the amino acid sequence or nucleic acid sequence exhibits at least 82% correspondence with the indicated sequence. In another embodiment, the amino acid sequence or nucleic acid sequence exhibits at least 85% correspondence with the indicated sequence. In another embodiment, the amino acid sequence or nucleic acid sequence exhibits at least 87% correspondence with the indicated sequence. In another embodiment, the amino acid sequence or nucleic acid sequence exhibits at least 90% correspondence with the indicated sequence. In another embodiment, the amino acid sequence or nucleic acid sequence exhibits at least 92% correspondence with the indicated sequence. In another embodiment, the amino acid sequence or nucleic acid sequence exhibits at least 95% or more correspondence with the indicated sequence. In another embodiment, the amino acid sequence or nucleic acid sequence exhibits at least 97% correspondence with the indicated sequence. In another embodiment, the amino acid sequence or nucleic acid sequence exhibits at least 99% correspondence with the indicated sequence. In another embodiment, the amino acid sequence or nucleic acid sequence exhibits 95-100% correspondence with the indicated sequence. Similarly, as used herein, the reference to a correspondence to a particular sequence includes both direct correspondence, as well as homology to that sequence as herein defined.

In another embodiment, homology refers to sequence identity, or in yet another embodiment, may refer to structural identity, or functional identity. By using the term "homology" and other like forms, it is to be understood that any molecule, whether nucleic acid or peptide, that functions similarly, and/or contains sequence identity, and/or is conserved structurally so that it approximates the reference sequence, is to be considered as part of this invention.

Protein and/or peptide homology for any peptide sequence listed herein may be determined by immunoblot analysis, or via computer algorithm analysis of amino acid sequences, utilizing any of a number of software packages available, via methods well known to one skilled in the art. Some of these packages may include the FASTA, BLAST, MPsrch or Scanps packages, and may employ the use of the Smith and Waterman algorithms, and/or global/local or BLOCKS alignments for analysis, for example.

The presence of long dsRNAs in cells stimulates, in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence.

The presence of long dsRNAs in cells stimulates, in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence.

In one embodiment, the siRNA of the gene encoding PCIF1 described herein exhibits substantial complementarity to its target sequence. In another embodiment, "complementarity" refers to an oligonucleotide has a base sequence containing an at least 15 contiguous base region that is at least 70% complementary, or in another embodiment at least 75% complementary, or in another embodiment at least 80% complementary, or in another embodiment at least 85% complementary, or in another embodiment at least 90% complementary, or in another embodiment at least 95% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the siRNA of the gene encoding PCIF1 described herein is sufficiently complimentary to its target sequence. In one embodiment, the term "Sufficiently complementary" refers to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

In one embodiment, minor groove-binding N-methyl pyrrole (Py) and N-methylimidazole (Im) polyamides (peptides) uniquely recognize each of the four Watson-Crick base pairs. Antiparallel pairing of imidazole with pyrrole (Im/Py) recognizes in one embodiment, a G-C base pair, whereas in another embodiment, a Py/Py pair recognizes either an A-T or T-A base pair. The binding constant and sequence-specificity of the Py-Im hairpin polyamides are similar to that of a transcription factor. Therefore, many genes are silenced, in other embodiments, by competitive binding of Py-Im hairpin polyamides to their regulatory sequences. Gene expression is controlled in one embodiment, by a combination of multiple common transcription factors. In one embodiment, inhibition of gene expression through the binding of Py-Im polyamides to regulatory sequences is unique to a specific gene, and contains part of the recognition sequence of the transcription factor together with the unique flanking sequences. In another embodiment, targeting Py-Im polyamide to the coding region is more straightforward when selecting a unique sequence. In one embodiment, the agent used to silence the gene encoding PCIF1 in the methods and compositions described herein, is Py-Im polyamide specific for the gene's coding region, or to regulatory sequences that is unique to the gene encoding PCIF1 in another embodiment. In one embodiment, the agent used to silence the gene encoding PCIF1 in the methods and compositions described herein, is a synthetic polyamide nucleic acid (PNA) specific for the coding region of the gene encoding variable region of an anti-desmoglein (anti-Dsg) pathogenic autoantibody, or to its unique regulatory sequences in another embodiment.

In one embodiment, the polyamides used in the compositions and methods described herein, which, in another embodiment are referred to as "peptide nucleic acid" (PNA) or "synthetic peptide nucleic acids", are alkylating Py-Im polyamides that show sequence-specific DNA alkylation. In another embodiment, alkylation of a template strand in the gene encoding PCIF1, by Py-Im polyamide-cyclopropylpyrroloindole (CPI) conjugates with a vinyl linker results in the production of truncated mRNA, effectively inhibiting transcription of PCIF1 in vitro. In one embodiment, Py-Im tetrahydro-cyclo-propabenzindolone (CBI) conjugates with indole linkers are the alkylating polyamides used as the agent capable of inhibiting the expression or function of PCIF1, because indole-CBI has increased chemical stability under acidic and basic conditions.

In another embodiment, oligodeoxynucleotides utilized in methods and compositions described herein inhibit cellular transcription by binding to duplex DNA to form a triple helix.

Due to the possibility of long-term inhibition of the gene product, oligodeoxynucleotides that can bind duplex DNA have advantages over those that bind mRNA or proteins. These oligodeoxynucleotides are called in one embodiment, triplex forming oligonucleotides (TFOs). By using DNA-specific TFOs, the inhibition of expression of several cellular genes has been demonstrated, including the oncogene, c-myc, the human immunodeficiency virus-1, the alpha chain of the interleukin 2 receptor, the epidermal growth factor receptor, the progesterone responsive gene and the mouse insulin receptor. In one embodiment, the oligonucleotides used in the methods and compositions described herein, can bind to duplex DNA and form triple helices in a sequence-specific manner and will silence expression or function of the gene encoding PCIF1.

In one embodiment, homopyrimidine DNA strand (triplex forming oligonucleotide, TFO) can bind to a homopurine/homopyrimide DNA duplex in the major groove by forming Hoogsteen base pairs with the homopurine strand. The Hoogsteen base pairing scheme mediates sequence specific recognition of the double stranded DNA by the TFO where in one embodiment, an AT base pair is recognized by a T; and a GC base pair by a C that is protonated at $N3^+$. In another embodiment, homopurine strands specifically form a DNA triplex in which the AT base pair is contacted by an A; and the GC base pair by a G. In one embodiment, the agent capable of inhibiting the expression or function of the gene encoding PCIF1 is a triple-helix-forming agent. In another embodiment, the triple-helix-forming agents are olygonucleotides. In one embodiment, oligonucleotide-mediated triplex formation prevent transcription factor binding to promoter sites and block mRNA synthesis in vitro and in vivo. In another embodiment, DNA intercalating or cross-linking agents are used to prolong oligonucleotide-duplex interactions.

In one embodiment, the term "TFO" or "triplex forming oligonucleotide" refers to the synthetic oligonucleotides of the present invention which are capable of forming a triple helix by binding in the major groove with a duplex DNA structure.

In another embodiment, the term "bases" refers to both the deoxyribonucleic acids and ribonucleic acids. The following abbreviations are used, "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods described herein, without changing the scope of the invention.

The term "nucleic acid" as used in connection with siRNA, refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribonucleic acids, and the like. In one embodiment, the siRNAs used in the compositions and methods of the invention, are nucleic acid sequences.

In one embodiment oligomeric antisense compounds, particularly oligonucleotides, are used in modulating the function of nucleic acid molecules encoding PCIF1, ultimately modulating the amount of the PCIF1 produced. This is accomplished by providing antisense compounds which specifically hybridize with one or more nucleic acids encoding PCIF1. In one embodiment, the terms "target nucleic acid" and "nucleic acid encoding PCIF1" encompass DNA encoding PCIF1, RNA (including pre-mRNA and mRNA) transcribed from such DNA, and also cDNA derived from such RNA. The specific hybridization of an oligomeric compound with its target nucleic acid interferes in another embodiment, with the normal function of the nucleic acid. The modulation of function of a target nucleic acid by compounds which specifically hybridize to it, is referred to in one embodiment as "antisense". In one embodiment, the functions of DNA to be interfered with using the antisense oligonucleotides described herein, which are used in the methods and compositions described herein, include replication and transcription. In another embodiment, functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of PCIF1. In one embodiment, inhibition of gene expression is preferred and mRNA is a preferred target. In one embodiment, since many genes have multiple transcripts, "inhibition" also includes an alteration in the ratio between gene products, such as alteration of mRNA splice products.

In one embodiment, specific nucleic acids are targeted for antisense. "Targeting" an antisense compound to a particular nucleic acid, in one embodiment, is a multistep process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent. In one embodiment, the target is a nucleic acid molecule encoding PCIF1. The targeting process also includes in another embodiment, determination of a site or sites within this gene for the antisense interaction to occur such that the desired effect, e.g., inhibition of expression of the protein such as PCIF1, will result. In one embodiment, an intragenic site is the region encompassing the translation initiation or termination codon of the open reading frame (ORF) of the gene. Since, the translation initiation codon is in one embodiment 5'-AUG (in transcribed mRNA molecules; 5'-ATG in the corresponding DNA molecule), the translation initiation codon is referred to in one embodiment as the "AUG codon," the "start codon" or the "AUG start codon". In another embodiment, a minority of genes have a translation initiation codon having the RNA sequence 5'-GUG, 5'-UUG or 5'-CUG, and 5'-AUA, 5'-ACG and 5'-CUG and have been shown to function in vivo. Thus, the terms "translation initiation codon" and "start codon" encompasses in other embodiments, many codon sequences, even though the initiator amino acid in each instance is typically methionine (in eukaryotes) or formylmethionine (in prokaryotes). In another embodiment, "start codon" and "translation initiation codon" refer to the codon or codons that are used in vivo to initiate translation of an mRNA molecule transcribed from a gene encoding PCIF1, regardless of the sequence(s) of such codons.

In certain embodiments, a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer in one embodiment, to a portion of such a mRNA or gene that encompasses from about 25 to about 50 contiguous nucleotides in either direction (i.e., 5' or 3') from a translation initiation codon. In another embodiment, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," refers in one embodiment to the region between the translation initiation codon and the translation termination codon, is a region which may be targeted effectively. Other target regions include in other embodiments, the 5' untranslated region (5'UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises in one embodiment, an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region is a preferred target region in one embodiment.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be target regions in one embodiment, and are particularly useful in situations where aberrant splicing is implicated in disease, or where an overproduction of a particular mRNA splice product is implicated in disease in other embodiment, such as DM type II or pancreatic agenesis. Aberrant fusion junctions due to rearrangements or deletions are also preferred targets. In one embodiment, introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect. In one embodiment, the term "hybridization" refers to hydrogen bonding, which may be Watson-Crick, Hoogsteen or reversed Hoogsteen hydrogen bonding, between complementary nucleoside or nucleotide bases. In one embodiment, adenine and thymine are complementary nucleotide bases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are used in one embodiment, as research reagents and diagnostics. In another embodiment, antisense oligonucleotides, which are able to inhibit gene expression, such as the gene encoding PCIF1, with extreme specificity, are used by those of ordinary skill to elucidate the function of particular genes. Antisense compounds are used in another embodiment, to distinguish between functions of various members of a biological pathway. Antisense modulation is, in one embodiment of the agents described in the methods and compositions described herein, being harnessed for research use.

In one embodiment, the specificity and sensitivity of antisense agents described herein, is also harnessed for therapeutic uses. Antisense oligonucleotides are employed in one embodiment, as therapeutic moieties in the treatment of disease states in animals and man. In one embodiment, antisense oligonucleotides are safely and effectively administered to humans. In one embodiment oligonucleotides are useful therapeutic modalities that can be configured to be useful in treatment regimes of cells, tissues and animals, especially humans.

In one embodiment, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the oligonucleotides used in the methods and compositions described herein, are synthetic peptide nucleic acids (PNAs) which interact with the nucleotide sequence encoding PCIF1, in a sequence-specific manner and silence its expression or function. In another embodiment, the oligonucleotides used in the methods and compositions described herein, are locked nucleic acid (LNA), which interact with the nucleotide sequence encoding PCIF1, forming a LNA/DNA co-polymer, in a sequence-specific manner and substantially silence expression or function of the gene encoding PCIF1.

In one embodiment, the term "locked nucleic acid" (LNA) refers to a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun. 1247); and Singh et al, (1998 Chem. Commun. 455). As with PNA, LNA exhibits greater thermal stability when paired with DNA, than do conventional DNA/DNA heteroduplexes. In one embodiment, LNA can be joined to DNA molecules by conventional techniques. Therefore, in one embodiment, LNA is to be preferred over PNA, for use in the agents of the methods and compositions described herein. In another embodiment, the target specific regions of the agent that is able to inhibit gene expression of PCIF1, may comprise LNA and/or PNA and the arm region comprise DNA, with the agent further comprising a destabilizing moiety.

In another embodiment, the agent capable of inhibiting expression or function of the gene encoding PCIF1, is an agPNA. In another embodiment, this antibody is referred to as antigenic PNA. In one embodiment, the gene encoding PCIF1, is PCIF1.

In one embodiment, PCIF1 affects the development or in one embodiment, the function of glucagon-producing alpha cells. Accordingly and in another embodiment, provided herein is a method of increasing glucagon-producing α-cell mass in a subject, comprising the step of contacting the cell with a composition comprising a nucleotide sequence capable of inhibiting the expression of a nucleotide sequence encoding PCIF1, thereby increasing glucagon-producing α-cell mass in a subject, wherein said composition comprises a siRNA, a polyamide, a triple-helix-forming agent, an antisense RNA, a synthetic peptide nucleic acids (PNAs), an agRNA, a LNA/DNA copolymer, a small molecule chemical compound, or a combination thereof. In one embodiment, increasing glucagon producing α-cell mass in the subject using the methods and compositions provided herein, is due to increased differentiation of new α cell formation from undifferentiated progenitors. In one embodiment contacting the cells in the methods provided herein is via intravenous administration. In another embodiment, contacting is via intramuscular administration. In another embodiment, contacting is via intraarticular administration. In another embodiment, contacting is via intranasal administration. In another embodiment, contacting is via transnasal administration. In another embodiment, contacting is via parenteral administration. In another embodiment, contacting is via oral administration. In another embodiment, contacting is via aerosolized administration. In another embodiment, contacting is via their combination administration.

In one embodiment, reduction of PCIF1 normalizes glucose tolerance in subjects expressing Pdx1. In another embodiment, PCIF1 insufficiency is able to normalize glucose tolerance in Pdx1+/− PCIF1 gt/+ mice, indicating in another embodiment, a genetic interaction between PCIF1 and Pdx1 and is consistent in another embodiment with the ability of PCIF1 to negatively regulate Pdx1 activity in cells. Accordingly and in one embodiment, provided herein is a method of treating glucose intolerance in a subject, comprising the step of inhibiting the expression or function of PCIF1 or an encoded protein thereof. In another embodiment, provided herein is a method of inhibiting or suppressing glucose intolerance in a subject, or In another embodiment, provided herein is a method of reducing symptoms associated with glucose intolerance in a subject, comprising the step of inhibiting the expression or function of PCIF1 or an encoded protein thereof. In one embodiment, the compositions provided hereinabove, are used for the method of treating glucose intolerance in a subject, comprising the step of inhibiting the expression or function of PCIF1 or an encoded protein thereof.

In one embodiment, glucose intolerance treated using the methods provided herein comprises diabetes mellitus type II, insulin resistance, hyperglycemia or a combination thereof. Diabetes, hyperglycaemia and impaired glucose tolerance are endocrine disorders characterised in one embodiment, by inadequate production or use of insulin, which affects the metabolism of carbohydrates, proteins, and lipids resulting in abnormal levels of glucose in the blood. Diabetes refers in one embodiment to a heterogeneous disease that can be classified into two major group: Type 1 diabetes (also known as Insulin-dependent diabetes, IDDM, type I, juvenile diabetes) and Type 2 diabetes (Noninsulin-dependent diabetes, NIDDM, type II, maturity-onset diabetes).

In another embodiment, the methods provided herein are effective in increasing endogenous levels of PDX-1 in embryonic stem cells. Accordingly and in another embodiment, provided herein is a method of increasing endogenous levels of PDX-1 in embryonic stem cells (ES) comprising the step of downregulating the expression of PCIF1 in the embryonic stem cells, thereby promoting of β-cell differentiation. In another embodiment, the term "stem cells" refers to undifferentiated or immature cells that can give rise to various specialised cell types. Once differentiated or induced to differentiate, stem cells can be used in another embodiment, to repair damaged and malfunctioning organs. The stem cells used in the methods provided herein are of embryonic origin in one embodiment, or adult origin in another embodiment. In the pancreas, stem cells are present in one embodiment within the adult tissue.

In one embodiment, embryonic stem cells can be isolated from the inner cell mass of pre-implantation embryos (ES cells) or from the primordial germ cells found in the genital ridges of post-implanted embryos (EG cells). When grown in special culture conditions such as spinner culture or hanging drops, both ES and EG cells aggregate to form embryoid bodies (EB). EBs are composed of various cell types similar to those present during embryogenesis. When cultured in appropriate media, EB can be used to generate in vitro differentiated phenotypes, such as extraembryonic endoderm, hematopoietic cells, neurons, cardiomyocytes, skeletal muscle cells, and vascular cells. In one embodiment, contacting the embryonic stem cells with a composition comprising a siRNA, a polyamide, a triple-helix-forming agent, an antisense RNA, a synthetic peptide nucleic acids (PNAs), an agRNA, a LNA/DNA copolymers, a small molecule chemical compounds, or a combination thereof capable of inhibiting the expression of a nucleotide sequence encoding PCIF1 results in differentiation of the stem cells to produce β-cells, by increasing endogenous levels of Pdx-1.

In one embodiment, downregulating the expression of PCIF1 gene using the compositions described herein, prevents degradation of PDX-1 protein levels in adult human β cells, thereby decreasing β cell apoptosis, increasing replication and differentiation.

In another embodiment, increasing the mass of β-cell using the methods and compositions described herein, enables the transplantation of smaller number of islet cells as a therapeutic in DM patients. Accordingly and in another embodiment, provided herein is a method of reducing the number of islets needed to achieve cure in a diabetic subject treated with islet transplantation, comprising the step of transplanting in the subject islet cells comprising downregulated PCIF1 expression or function, thereby increasing β-cell mass.

Pancreatic islet replacement has been promoted as offering a "cure" for diabetes. Successful islet transplantation has been vigorously pursued for its potential in the complete control of glucose (i.e. a system with balanced glucose sensing and insulin secretion). In one embodiment, insulin secretion from transplanted islets is delayed and diminished when compared with secretion from a normal or transplanted pancreas. In one embodiment, ex-vivo treatment of islet cells using the methods and composition provided herein, increases transplanted cell insulin secretion, or in another embodiment, shortens the delay in insulin secretion by transplanted islet cells.

In one embodiment, provided herein is a method of screening a set of compounds for a compound capable of modulating β cell mass. In another embodiment, provided herein is a method of screening a set of compounds for a compound capable of increasing new β cell differentiation from progenitor cells. In another embodiment, provided herein is a method of screening a set of compounds for a compound capable of decreasing β cell apoptosis. In another embodiment, provided herein is a method of screening a set of compounds for a compound capable of increasing replication of existing β cells. In another embodiment, provided herein is a method of screening a set of compounds for a compound capable of increasing differentiation of new α cells from progenitor cells. In another embodiment, provided herein is a method of screening a set of compounds for a compound capable of their combination. In another embodiment, provided herein is a method of screening a set of compounds comprising the steps of: contacting a β cell with a candidate compound; and analyzing the β cell for the expression of PCIF1 gene, or capability of its encoded protein to bind to PDX-1, whereby a candidate compound capable of inhibiting the expression of PCIF1 gene, or capability of its encoded protein to bind to PDX-1 is a candidate compound for increasing β cell mass, increasing new β cell differentiation from progenitor cells, decreasing β cell apoptosis, increasing replication of existing β cells, increasing differentiation of new α cells from progenitor cells, or their combination. In another embodiment, the compositions provided herein, which are used in the methods provided herein, comprise a compound identified or isolated by the screening methods provided herein.

In one embodiment, contacting a β cell with a candidate compound whereby contacting is via intravenous administration. In another embodiment, contacting is via intramuscular administration. In another embodiment, contacting is via intraarticular administration. In another embodiment, contacting is via intranasal administration. In another embodiment, contacting is via transnasal administration. In another embodiment, contacting is via parenteral administration. In another embodiment, contacting is via oral administration. In another embodiment, contacting is via aerosolized administration. In another embodiment, contacting is via their combination administration. In one embodiment, the β-cell is in a transgenic mouse which is modified to overexpress PCIF1. In another embodiment, the transgenic mouse does not express PCIF1, or Pdx-1 in another embodiment, or any combination thereof in another embodiment.

In one embodiment, contacting the cell of the subject with the compositions provided herein, as used in the methods provided herein, comprises harvesting a progenitor cell from the subject, inducing β-cell differentiation; increasing β-cell mass of the differentiated cell; and returning the β-cells to the subject.

In one embodiment, provided herein is a method of treating congenital hyperinsulinism (CHI) in a subject, comprising the step of contacting the subject with a composition comprising a compound capable of increasing the expression of PCIF1 or its function in the subject. Congenital hyperinsulinism (CHI) refers in one embodiment to a disease characterized by persistent insulin secretion despite life-threatening hypoglycemia. The severity of the disease varies from a mild form, which responds to treatment with drugs (such as diazoxide) or hormones (like somatostatin), to a severe drug-resistant form, which may necessitate resection of the pancreas. Early diagnosis is important to avoid irreversible brain damage due to prolonged hypoglycemia. In one embodiment, the methods provided herein using the compositions capable of increasing the expression of PCIF1 in one embodiment, or bind PDX-1 in another embodiment, are effective in the treatment of refractive CHI.

In one embodiment, ubiquitin-proteasome pathway plays a role in the biogenesis efficiency and surface expression of β-cell $K_{ATP}$ channels. ATP-sensitive potassium ($K_{ATP}$) channels of pancreatic β-cells mediate glucose-induced insulin secretion by linking glucose metabolism to membrane excitability. The number of plasma membrane $K_{ATP}$ channels determines the sensitivity of β-cells to glucose stimulation. In another embodiment, proteasome inhibitors promote $K_{ATP}$ channel surface expression by increasing channel biogenesis efficiency rather than affecting other cellular events. In one embodiment, dominant or recessive mutations in ABCC8 or KCNJ11 that reduce or abolish channel activity are the major genetic cause of the disease. In another embodiment, overexpression of PCIF1 and cullin-3 promotes Pdx1 degradation by proteasome. In another embodiment Pdx1 expression is reduced in the setting of PCIF1/cullin-3 over-expression and this reduction is attenuated by co-administration of MG132, an established proteasome inhibitor. In one embodiment overexpression of PCIF1/cullin-3 results in targeting of Pdx1 to the proteasome for degradation, occupying proteasome in the cell, and decrease PDX-1 in another embodiment, thereby shifting in one embodiment, the equilibrium towards channel assembly.

Therefore, in one embodiment, provided herein is a method of treating congenital hyperinsulinism (CHI) in a subject, comprising the step of contacting the subject with a composition comprising a compound capable of increasing the expression of PCIF1 or its function, PCIF1, a compound capable of inhibiting the expression of a nucleotide sequence encoding Pdx-1, an anti-PDX-1 antibody, a compound identified or isolated using the screening methods provided herein, or their combination.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

Constructs

Expression vectors were full length mouse PDX-1, mouse PDX-1(1-210), pGBKT7-PDX-1(144-283) and GST-PDX-1 (206-283), rat PDX-1, human PDX-1, zebrafish PDX-1, Flag-PCIF1, Gal-PDX-1, Gal-4 BCL6 POZ and Gal-4 PLZF POZ, human PDX-1 wild-type and E224K and GST-TRAF and GST-POZ, Reporters were the PDX-1-responsive somatostatin promoter reporter $(TAAT)_s$ 65 SMS-CAT and the Gal-4-responsive reporters G51bCAT and Gal4SV40Luc.

Flag-tagged mutants of PCIF1 and Gal4-FCIF constructs were created by PCR. All constructs were confirmed by sequencing.

Immunoprecipitation and Western-Blot Analysis

Mouse insulinoma cell line 6 (MIN6) cells ware lysed in 150 mM NaCl, 40 mM Tris-HCl, pH 7.6, 10% glycerol and 0.3% NP-40 and immunoprecipitations ware carried out. Primary antisera were: HDAC3 (mouse, gift from M. Lazar) and HDAC3 (Santa Cruz: #sc11417); HDAC3 (Santa Cruz #sc-7899); SMRT (mouse, gift from Mitch Lazar) and SMRT (ABR, # PAI-842).

Transfection

HeLa cells were transfected with expression and reporter vectors and an internal control cmv-β galactosidase expression vector, Chloram-phenicol acetyl transferase, luciferase and β galactosidase activities were measured.

GST Interactions Assays

Bacterially expressed GST fusion proteins were incubated with in vitro-transcribed and -translated $^{35}$S-labelled full length PDX1, PDX1(1-21D), PDX1(Δ21O-238), PDX1 (144-283). After washing, proteins bound to glutathione beads were analyzed by SDS-PAGE.

Immunofluorescence

Transfected cells were stained with a Flag monoclonal antibody.

Example 1

PCIF1 Inhibits PDX-1 Transactivation

Figure 1:
FIG. 1 shows identification of PCIF1, a novel nuclear protein that inhibits PDX-1 transactivation. Diagram depicting the domain structure of PCIF1.

To gain insight into the regulation of PDX-1, the PDX-1 C-terminus was investigated as a protein-protein interaction domain by yeast two-hybrid analysis. Using the PDX-1 C-terminus (AA 206-283) as bait to screen a mouse embryonic day 17 library yielded a clone that was called PCIF1 (PDX C-terminus Interacting Factor-1) (FIG. 1). The physical interaction between PCIF1 and PDX-1 was confirmed in vitro by GST pulldown assay and in vivo by co-immunoprecipitation (coIP). In transfected HeLa cells, PCIF1 is localized to the nucleus in a speckled pattern, and co-expression of PDX-1 alters the subnuclear distribution of PCIF1. Functionally, PCIF1 inhibits PDX-1 transactivation of established target gene promoters in a specific and dose-dependent manner that requires critical amino acids in the PDX-1 C-terminus. PCIF1 mRNA is enriched in adult pancreas, and PCIF1 protein is expressed in adult pancreatic insulin-producing β cells. Finally, over-expression of PCIF1 inhibits the rat insulin 1 and rat insulin 2 promoters in the MIN6 insulinoma β cell line. The co-expression of PCIF1 with PDX-1 in β cells and its ability to repress PDX-1 transactivation indicate that PCIF1 modulation of PDX-1 function regulates β-cell differentiation.

PCIF1 encodes a protein of 374 amino acids with a predicted molecular weight of 42 kDa and contains an N-terminal TRAF domain (AA 36-142) and a typical POZ domain (AA 190-297) (FIG. 1). A BLAST search of the PCIF1 clone identified its human homolog as SPOP (speckle-type POZ protein), a widely expressed nuclear protein of unknown function identified in an expression screen using the serum of a scleroderma patient. PCIF1 is highly conserved, sharing 100% amino acid identity with human SPOP. PCIF1 homologs are present in the *D. rerio* (zebrafish), *D. melanogaster* and *C. elegans* databases. The prey plasmid encodes AA 46-374, which includes a portion of the TRAF and the entire POZ and C-terminal domains.

The POZ domain is an evolutionarily conserved protein-protein interaction motif, found in diverse proteins including transcription factors, oncogenic proteins, ion channel proteins, and some actin-associated proteins. The most-well characterized POZ domain transcription factors are the human oncogenes PLZF and BCL-6. PLZF (promyelocyte leukemia zinc finger) translocations have been found in humans with acute promyelocytic leukemia; these translocations result in the fusion of the PLZF POZ domain and two of its nine zinc fingers with the retinoic acid receptor (RARα) gene, which results in POZ-domain mediated recruitment of a histone deacetylase complex and resultant abnormal repression of RARα target promoters. Recruitment of HDAC/co-repressor complexes to the POZ domain has been demonstrated for a number of other POZ domain transcription factors, including BCL-6, supporting this as a general mechanism for POZ-mediated transcriptional repression.

The TRAF (TNF Receptor-Associated Factor) domain was originally defined in a family of adapter proteins that bind to the cytosolic tail of TNF receptors. TRAF domains are typically found at the C-terminus, and they mediate both homotrimeric interactions and heterocomplex formation with TNF receptors, other adaptor proteins, kinases and inhibitor of apoptosis (IAP) homologs. The PCIF1/SPOP TRAF domain is atypically located at the N-terminus and does not self-associate, although it does interact weakly in vitro with the related domains from TRAF1 and TRAF6. Deletion of the TRAF domain from SPOP causes a relocation of SPOP from nuclear speckles to a diffuse nuclear distribution. SPOP in a yeast two hybrid screen for proteins was identified, which interact with the distinctive C-terminal domain of macroH2A1.2, a variant histone that is enriched in, although not exclusively localized to, the inactive X chromosome. In addition to the POZ domain, the PCIF1 TRAF domain could be involved in mediating repression, via effects on subnuclear localization of PCIF1 and potentially through modification of chromatin structure.

In considering whether PCIF1 could regulate PDX-1 protein stability by enhancing ubiquitination and degradation, PDX-1 expression levels were closely followed and an alteration in PDX-1 molecular weight or expression level were not observed in the presence of PCIF1. PCIF1 is the first protein identified to interact with the C-terminus of PDX-1, and it is the first partner that directly represses PDX-1 transactivation. The data show that while PCIF1 is expressed in adult pancreatic insulin-producing β cells, its expression domain during embryonic development indicates a broader role in the differentiation of the endocrine pancreas. Modulation of PCIF1 in a β cell line (MIN6) influences insulin promoter activity, indicating that PCIF1 expression level and/or its ability to interact with PDX-1 is a determinant of insulin gene transcription rate. Domain mapping studies indicate that inhibition by PCIF1 is mediated by a short conserved peptide sequence in the PDX-1 C-terminus and that the PCIF1 POZ domain is critically required for inhibition.

Example 2

Endogenous PCIF1 is Expressed in Pancreas and MIN6 Cells

Figure 2:
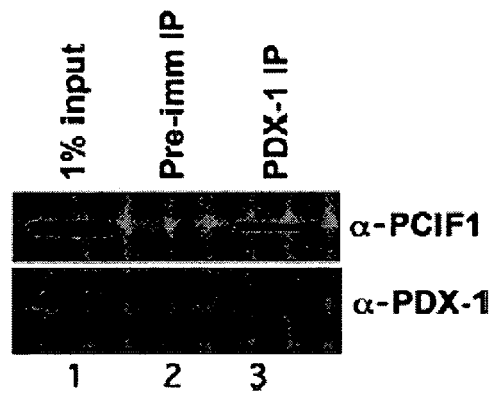
FIG. 2 shows interaction of endogenous PDX-1 and PCIF1 in MIN6 insulinoma cells. Cell extracts were immunoprecipitated with α-PDX1 and immunoblotted with α-PDX1 and α-PCIF1. Lane 1, 2% of input extract; Lane 2, pre-immune IP; Lane 3. α-PDX-1 IP.

An in vivo association of endogenous PDX-1 and PCIF1 proteins is also demonstrated in MIN6 (FIG. 2) and βTC-3 protein extracts. Immunoprecipitation of MIN6 extracts with α-PCIF1 cross-linked to agarose beads resulted in the co-IP of PDX-1 (lane 3), whereas pre-immune control IgG did not (lane 2). The interaction in MIN6 cells is reproducible and specific but weak, which we can now attribute to the low level of PCIF1 expression in MIN6 cells compared with primary pancreatic tissue. The reverse co-IP using α-PDX-1 to IP and α-PCIF1 to detect remains problematic.

Example 3

PCIF1 is Expressed During Late Embryonic Pancreas Development

Figure 3:
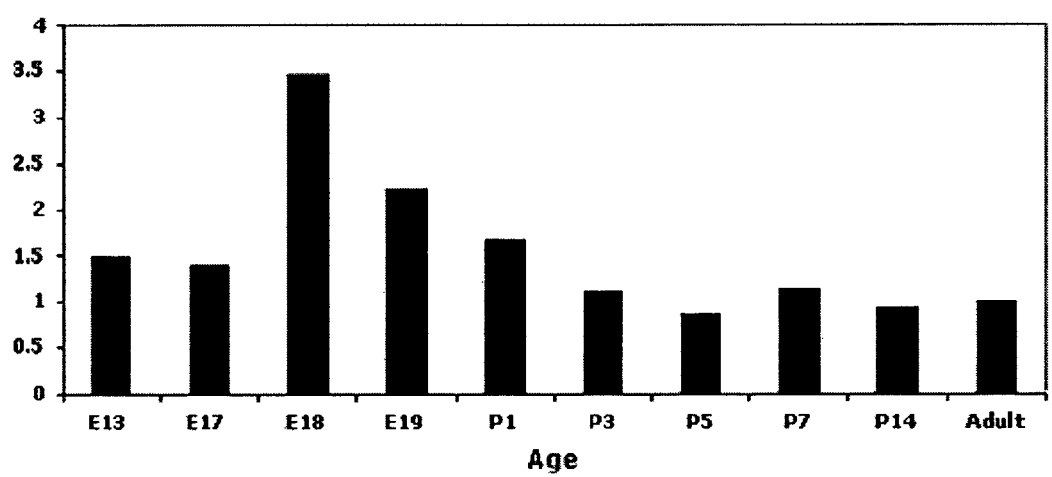
FIG. 3 shows PCIF1 mRNA levels during pancreas development. Total RNA isolated from pancreas at the ages indicated, reverse-transcribed and assessed for PCIF1 mRNA by quantitative real time PCR. Data normalized to actual cDNA input, as measured on a Nanophot apparatus. The peak at E18 remains when the data are normalized to HPRT or TBP.

To correlate protein levels with mRNA levels, quantitative real time PCR primers for PCIF1 were developed. Total RNA was isolated from mouse pancreas at the same embryonic and postnatal time points. PCIF1 mRNA was expressed throughout development but was enriched in E18-E19 pancreas (~3.5 fold enriched at E18 c/w adult pancreas) (FIG. 3). This peak precedes the peak of PCIF1 protein expression by 24 hours, further validating the Western blot detection of PCIF1. We note a discrepancy between PCIF1 protein and mRNA levels at E13-E15, indicating a post-transcriptional level of control.

Example 4

Effective PCIF1 siRNA Inhibits PDX-1 Transactivation

Figure 4:
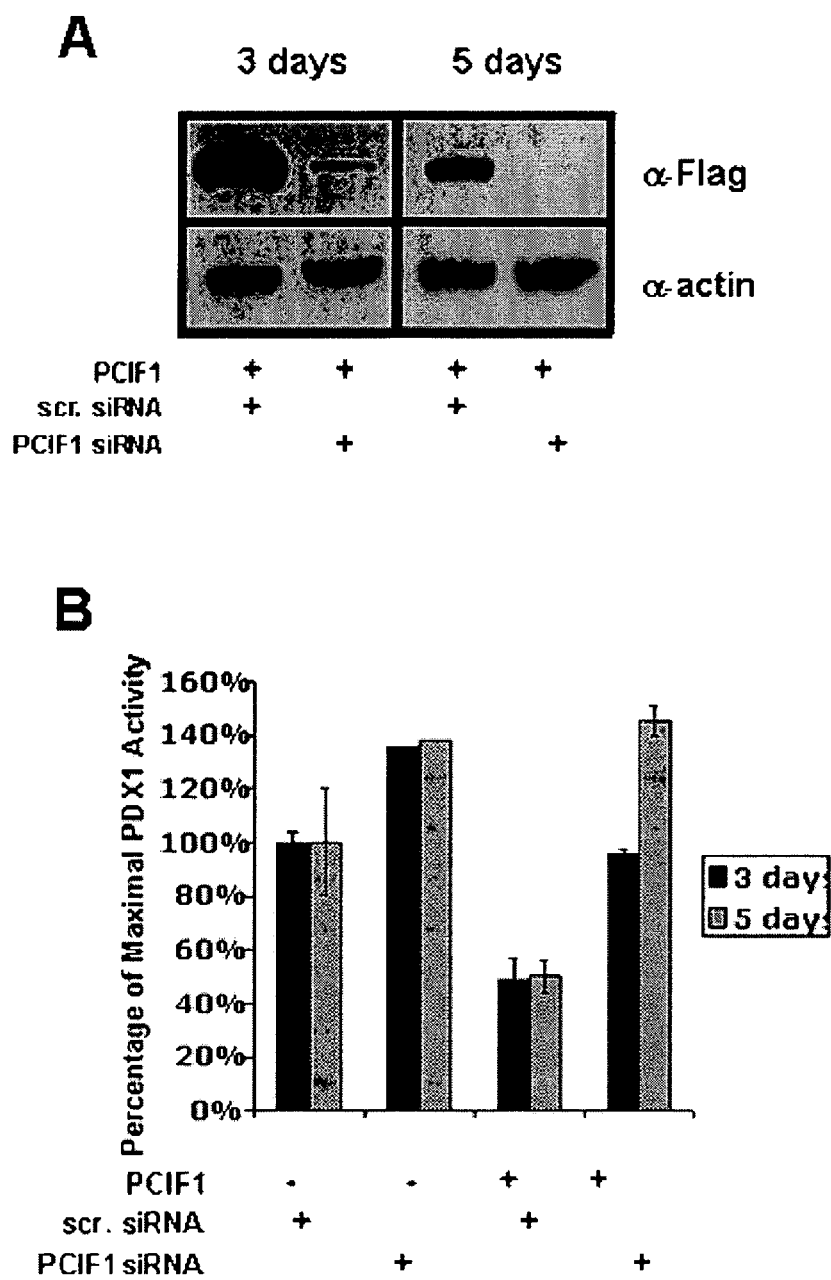
FIG. 4 shows development of an effective PCIF1 siRNA. Co-transfection of scrambled (scr) control or PCIF1 siRNA plasmid with Flag-PCIF1, Gal4-PDX-1 and G51BCAT in HeLa cells. (A) Western blot analysis for PCIF1 and actin (loading control) of protein extracts harvested at 3 and 5 days after transfection. (B) Gal4 reporter activity normalized for internal control β-galactosidase activity.

The efficacy of a PCIF1 siRNA to reduce PCIF1 expression was tested. The siRNA was subcloned into the 2.1-U6 neo pSilencer vector (Ambion) and co-transfected to HeLa cells with PCIF1. As shown in FIG. 4, PCIF1 was well-expressed in the presence of a pSilencer plasmid expressing a scrambled control siRNA. In contrast, PCIF1 protein was markedly reduced 3 days after co-transfection with the PCIF1 siRNA containing plasmid. The effect was more pronounced at 5 days, when PCIF1 protein could no longer be detected (FIG. 4A).

The effect of this siRNA on PCIF1 function was examined. HeLa cells were co-transfected with Gal4-PDX-1, the Gal4 reporter G51BCAT, PCIF1 and either control or PCIF1 siRNA plasmid. Control scrambled siRNA had no effect on the ability of PCIF1 to inhibit PDX-1 transactivation (~60%; FIG. 4B). In contrast, PCIF1 siRNA augmented Gal4-PDX1 activity in both the presence and absence of co-transfected PCIF1, indicating the efficacy of PCIF1 siRNA to block PCIF1 function and further indicate that endogenous PCIF1 contributes to PDX-1 activity in transfected HeLa cells. PCIF1 siRNA restored PDX-1 transactivation in the presence of PCIF1 to normal levels by 3 days and was maximal by 5 days. With an effective PCIF1 siRNA already based in a plasmid vector, its now possible to determine the effect of PCIF1 deficiency in 8 cell lines.

Example 5

Figure 5:
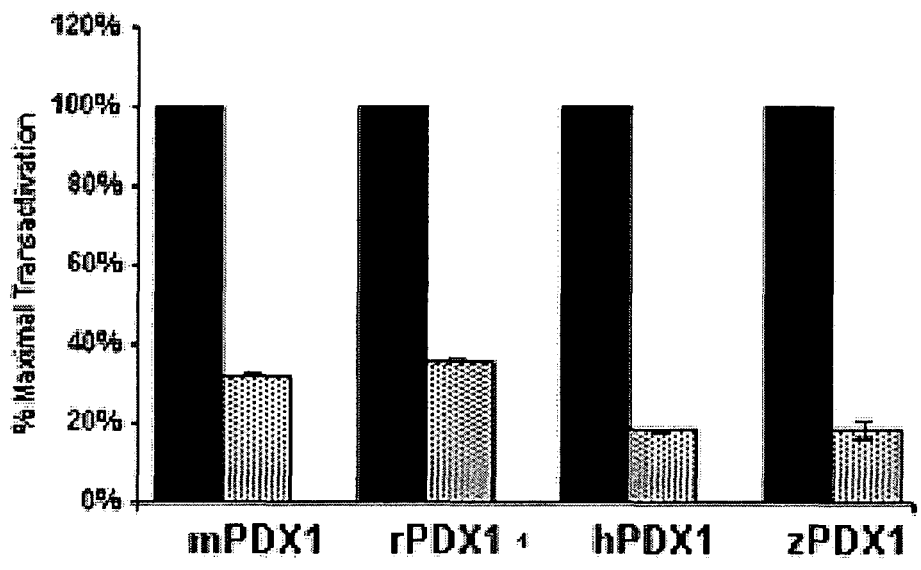
FIG. 5 shows evolutionary conservation of PCIF1 function. Transactivation was tested in transient transfection assays in HeLa cells using the SMS(TAAT1)$_5$CAT reporter. The activity of each PDX homolog (mouse, rat, human and zebrafish) in the absence of PCIF1 was set to 100% (black boxes), for comparison to activity in the presence of PCIF1 (shaded boxes)
Figure 6:
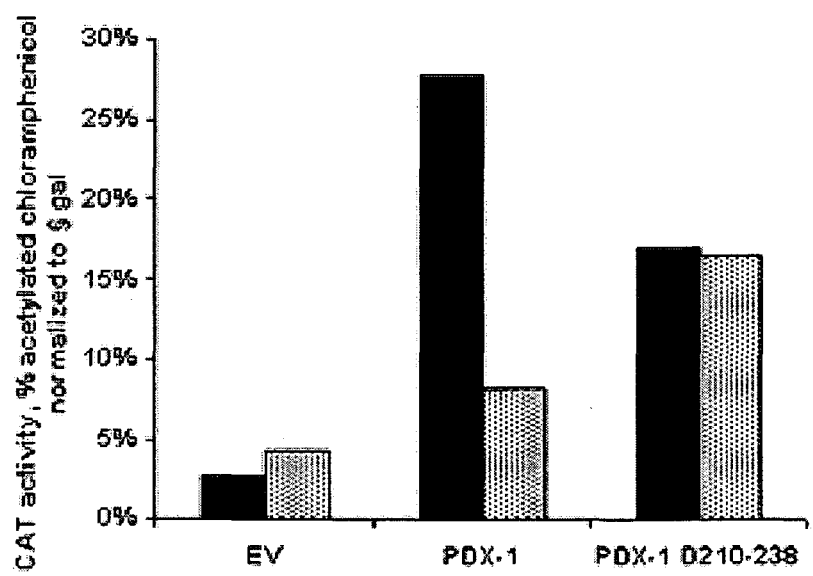
FIG. 6 shows internal deletion of AA 210-238 abrogates PCIF1 repression of PDX-1 transacti-vation. The activity of mPDX-1 Δ210-238 was compared to wild-type mPDX-1 in the absence (black boxes) and presence (shaded boxes) of co-transfected PCIF1. Transfections carried out in HeLa cells, using the SMS(TAAT1)$_5$CAT reporter. N=3.
Figure 10:
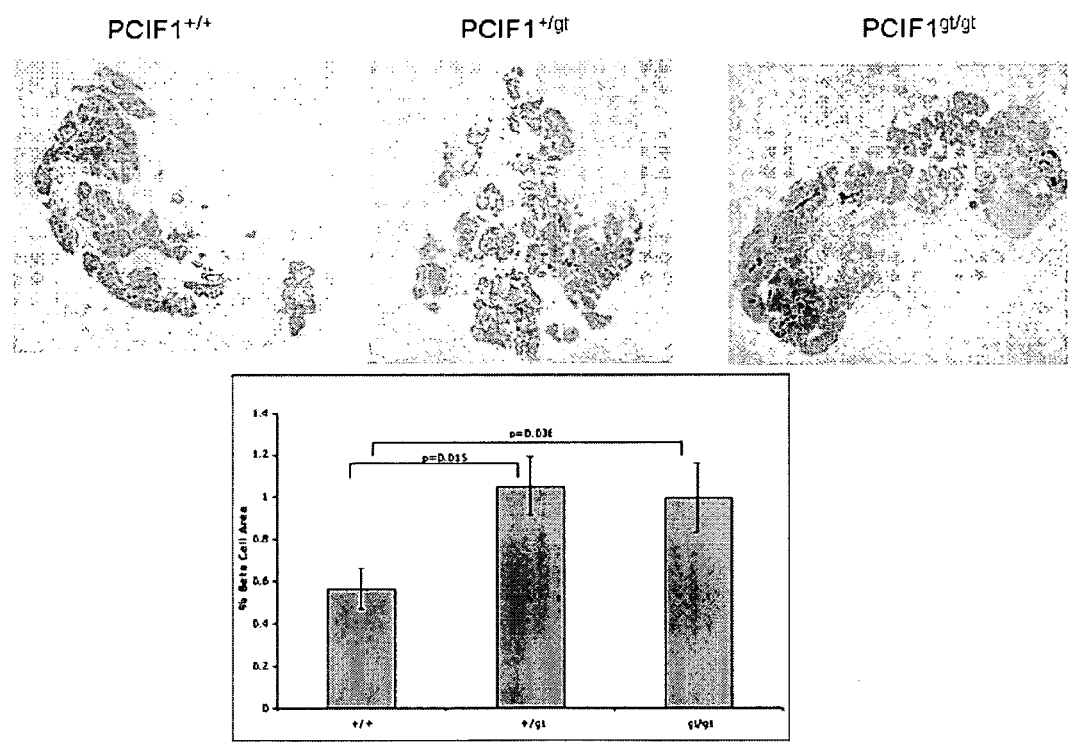
FIG. 10 shows heterozygous and homozygous PCIF1$^{gt/gt}$ and PCIF1$^{gt/+}$ mice of both genders have about double the b-cell area of PCIF1$^{+/+}$ mice.

Functional Interaction with PCIF1 Requires Evolutionarily Conserved AA 210-238 of the PDX-1 C-Terminus Since PCIF1 binds to the C-terminus of PDX-1, it was hypothesized that the C-terminus would be required for repression of PDX-1 activity by PCIF1. Indeed, the ability of PCIF1 to inhibit transactivation was completely abrogated with the deletion of the PDX-1 C-terminus in two independent PDX-1 reporter assays. The functional interaction of PCIF1 with PDX-1 is also conserved during evolution. Mouse PCIF1 similarly inhibited transactivation by mouse, rat, human and zebrafish homologs of PDX-1 (FIG. 5), indicating that PCIF1 interacts with a conserved motif in PDX1. Comparison of the C-terminus from multiple species reveals a highly conserved 14 AA motif (FIG. 10). Remarkably, deletion of amino acids 210-238, which includes this conserved motif, from Gal4-PDX-1 (1-238) completely abrogated repression by PCIF1. Similarly, when AA 210-238 are internally deleted from mouse PDX-1, the ability of PCIF1 to repress PDX-1 transactivation was lost (FIG. 6). In both assays, the loss of these amino acids was also associated with an modest overall reduction in transactivation. Thus, amino acids 210-238 of PDX-1 encoding the proximal portion of the C-terminus are essential for PCIF1 inhibition of PDX-1 activation. These functional data are in agreement with GST pull down assays indicating that the C-terminus of PDX-1 mediates the physical interaction with PCIF1.

Example 6

PCIF1 Specifically Inhibits PDX-1 Transactivation

Figure 7:
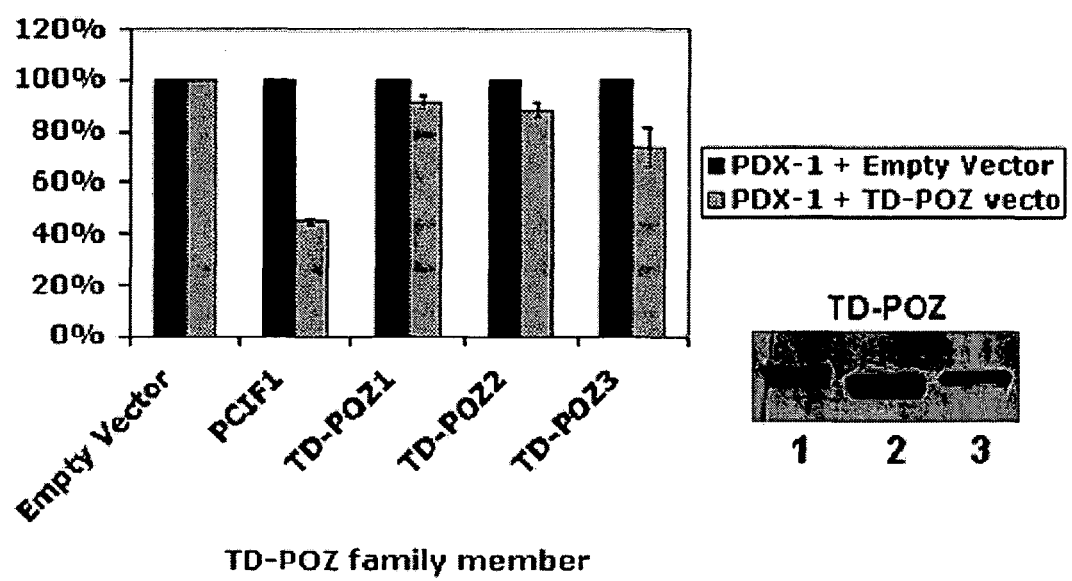
FIG. 7 shows that TD-POZ 1, 2 and 3 do not mimic the ability of PCIF1 to inhibit PDX-1 transactivation. Mouse PDX-1 was co-transfected with empty vector or Flag tagged mouse PCIF1. TD-POZ 1, 2 or 3 and the SMS(TAAT1)$_5$CAT reporter. N=2. Insert, Western blot analysis using Flag antibody, showing expression of all TD-POZ forms.

The mouse TD-POZ gene family encompasses 8 intronless genes that encode proteins with an identical overall domain structure to PCIF1. To date, only the early expression pattern of TD-POZ genes in 2 cell embryos have been described. To assess the specificity of PCIF1 in inhibiting PDX-1, the effect of 3 highly homologous TD-POZ proteins on PDX-1 transactivation was examined. The coding regions of TD-POZ 1, 2 and 3 were cloned into the pcmx-Flag. All were well-expressed; however, none were effective to inhibit PDX-1 transactivation, except for a weak inhibitory effect of TD-POZ 3 (FIG. 7). Further, the distantly related POZ domain protein PLZF also has no effect on PDX-1 transactivation (data not shown). These results indicate the specificity of PCIF1, and they also provide important comparative sequence information that can be used to refine the PCIF1 amino acid sequences critical for its ability to inhibit PDX-1 transactivation.

Example 7

Figure 8:
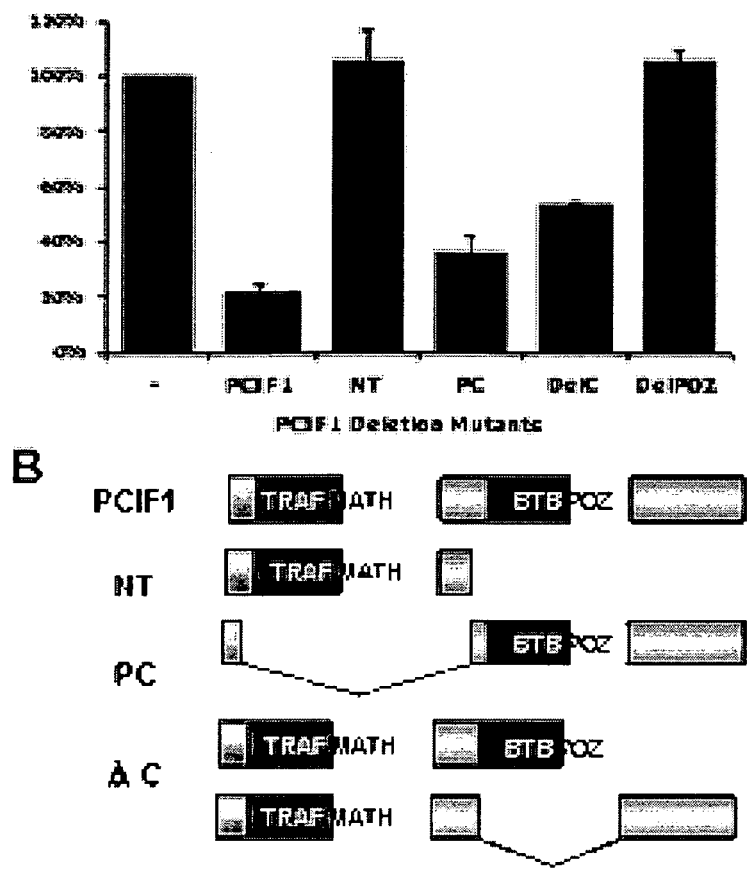
FIG. 8 shows PCIF1 deletion mutants reveal critical importance of the POZ domain for inhibition of PDX-1 transactivation. Overlap PCR was used to create Flag tagged PCIF1 deletion mutants, outlined in (B). (A) Mutants were tested in transient transfection assays for the ability to inhibit Gal4-PDX-1 transactivation of the G51B CAT reporter (n=2-5 exp'ts). Transactivation of Gal4-PDX-1 in the absence of PCIF1 is set to 100%. (C) GST pull-down assay using GST PDX 206-283 to pull-down $^{35}$S-labelled in vitro transcribed/translated full-length PCIF1 (FL) and mutants NT and PC.

The POZ Domain is Critically Required for PCIF1 Inhibition of PDX-1 Transactivation To determine which regions of PCIF1 are required for interaction with and inhibition of PDX-1, deletion mutants of PCIF1 were created in which the TRAF, POZ or C-terminal domains were removed (FIG. 8B). All mutants expressed well in HeLa cells based on Western blot analysis, except for the NT mutant, which could be detected but at significantly lower levels than full length PCIF1. The NT mutant also mislocalizes to the cytoplasm when visualized by immunofluorescence staining. The lack of inhibition by the NT mutant may thus relate to its inability to physically interact with PDX-1 (FIG. 8C) as well as to its low level of expression and inappropriate subcellular distribution in transfected cells. Deletion of the C-terminus (AC mutant) and TRAF (PC mutant) domains did not significantly impair PCIF1 inhibition of PDX-1. In contrast, internal deletion of the POZ domain completely abrogated the ability of PCIF1 to inhibit PDX-1 transactivation, (FIG. 8A). GST pull-down assays using the PC and NT mutants indicate that the sequences required for PDX-1 interaction are located in the POZ or C-terminal domains (FIG. 8C). Further, the residual inhibition by the AC construct supports the hypothesis that the POZ domain contains the PDX-1 interaction motif (FIG. 8A). Taken together, the data indicate a critical role for the POZ domain in PCIF1-mediated inhibition and likely also in the physical interaction with PDX-1, while TRAF and C-terminus may contribute to full inhibition by PCIF1.

Example 8

PCIF1 Inhibits Insulin Promoter Activity in MIN6 Cells

Figure 9:
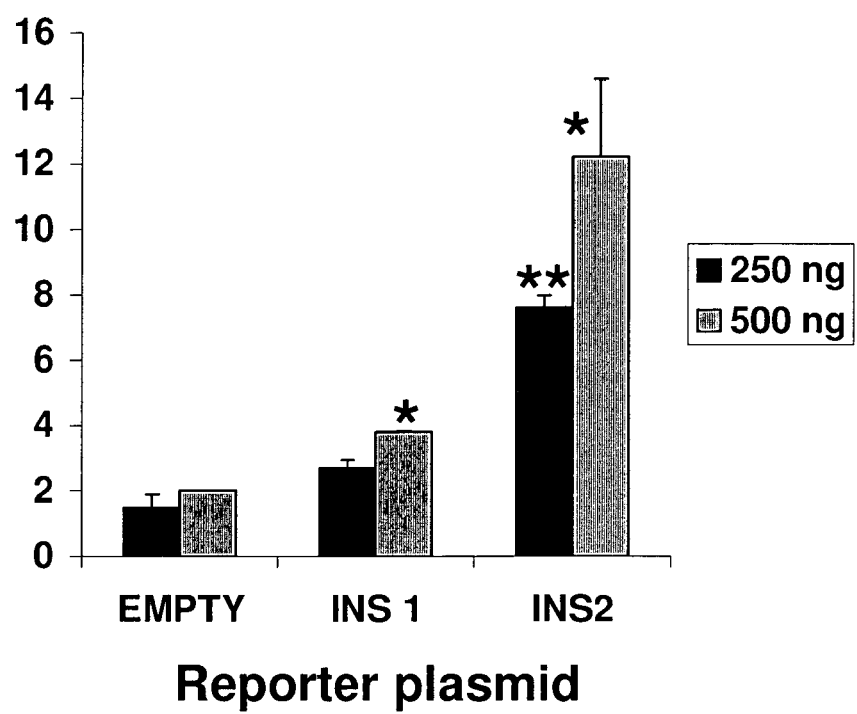
FIG. 9 shows that PCIF1 represses the insulin promoter in the MIN6 cells. Insulin promoter reporters rat INS1 CAT and rat INS2 CAT were transfected into MIN6 cells in the presence of varying amounts of PCIF1 expression vector (0, 250 and 500 ng). Data are normalized to internal control β galactosidase activity, and fold repression relative to 0 ng PCIF1 is presented. N=2±SEM. Each experiment was carried out in triplicate. *p<0.05, **p<0.005.

Next it was determined whether PCIF1 represses insulin gene transcription in β cells using the intact insulin promoter reporters, rat INS1 CAT and rat INS2 CAT, in MIN6 cells. The rat INS1 promoter had greater basal activity than the rat INS2 promoter. A dose-dependent inhibition of both reporters by PCIF1 (FIG. 9) was observed. Similar results were observed in the βTC-3 insulinoma line. Of note, the rat insulin 2 promoter was more sensitive to repression by PCIF1, which may relate to the presence of fewer homeodomain binding A box elements and specifically the presence of only one A/E box enhancer (Nir-P1) in the rat insulin 2 promoter compared to the two enhancers (Nir-P1 and Far-FLAT) present in the rat insulin 1 promoter. Similar assays were carried out with the PCIF1 domain deletions depicted in FIG. 8B. In contrast to its preserved inhibition of Gal4-PDX-1 activity in heterologous cells, the PC mutant was not only unable to inhibit the insulin promoter, it further increased insulin promoter activity 160%, indicative of a weak dominant negative effect on insulin promoter activity. These experiments were carried out in MIN6 cells grown in high glucose. Together, the data indicate that PCIF1 can modulate insulin promoter activity in β cell lines, and are consistent with an in vivo role for PCIF1 in modulating insulin gene expression.

Example 9

Reduction in PCIF1 Results in Expansion of β-Cell Area

A gene trap mouse allele that disrupts the expression of PCIF1 was generated using ES cells targeted by retroviral insertion of a strong splice acceptor cassette within the first large non-coding intron of PCIF1. Blastocysts were injected, chimeras were generated, and germ line transmission was achieved. Heterozygous and homozygous $PCIF1^{gt/gt}$ and $PCIF1^{gt/+}$ mice of both genders are born in roughly the expected Mendelian frequencies. Heterozygous mice appear normal at birth, grow normally postnatally and are fertile. Homozygous mice die on postnatal day. Preliminary evaluation of lung and pancreas RNA indicates a >99% reduction in PCIF1 mRNA. It was demonstrated that the remaining exons of PCIF1 remain intact in genomic DNA from homozygous mutant mice. Assessment of pancreatic islet architecture show heterozygous and homozygous $PCIF1^{gt/gt}$ and $PCIF1^{gt/+}$ mice of both genders have about double the β-cell area of $PCIF1^{+/+}$ mice. (see FIG. 10).

Figure 12:
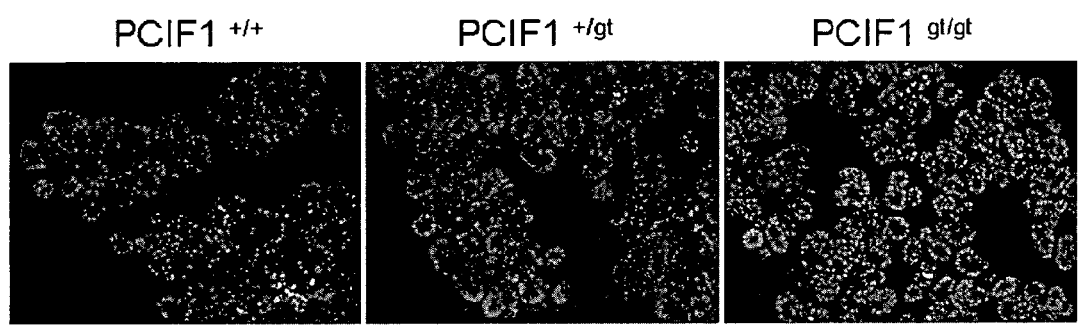
FIG. 12 shows increased PDX-1 level in PCIF1$^{gt/gt}$ mice.
Figure 16:
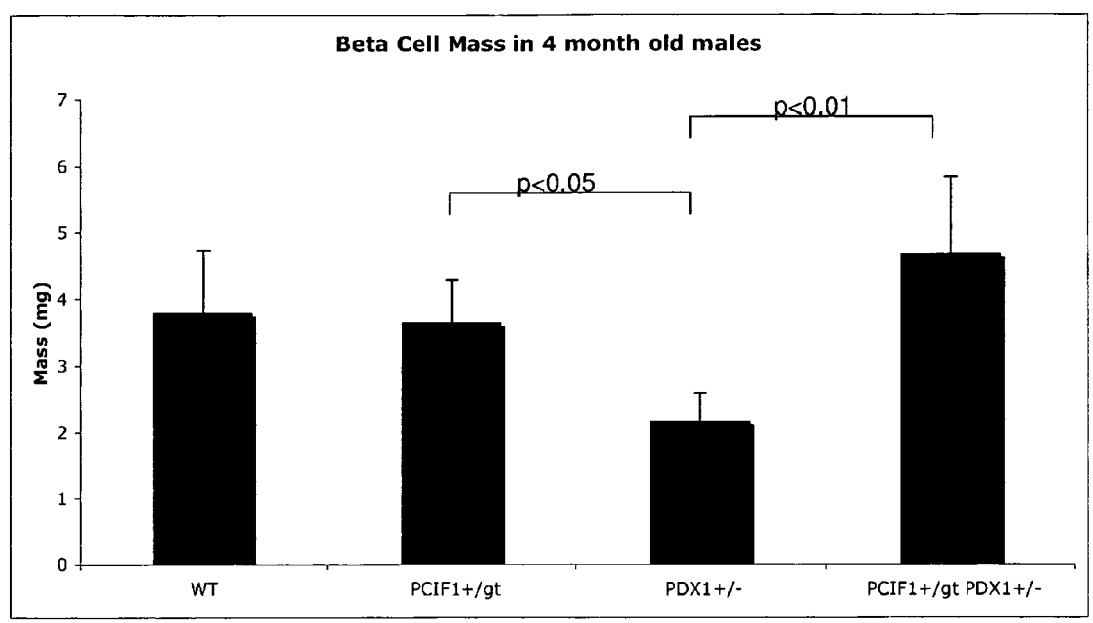
FIG. 16 shows β-cell mass in 4 year old males.

In addition, reduction in the expression of PCIF1 was demonstrated to delay acinar development in pancreatic cells (FIG. 11), indicating the effect of PCIF1 on cell differentiation by stabilizing levels of PDX-1 (see FIG. 12). Likewise see effect of the reduction in PCIF1 and PDX-1 stabilization on β-cell mass in 4 month old males (FIG. 16)

Example 10

Reduction of PCIF1 Normalizes Glucose Tolerance

Figure 13:
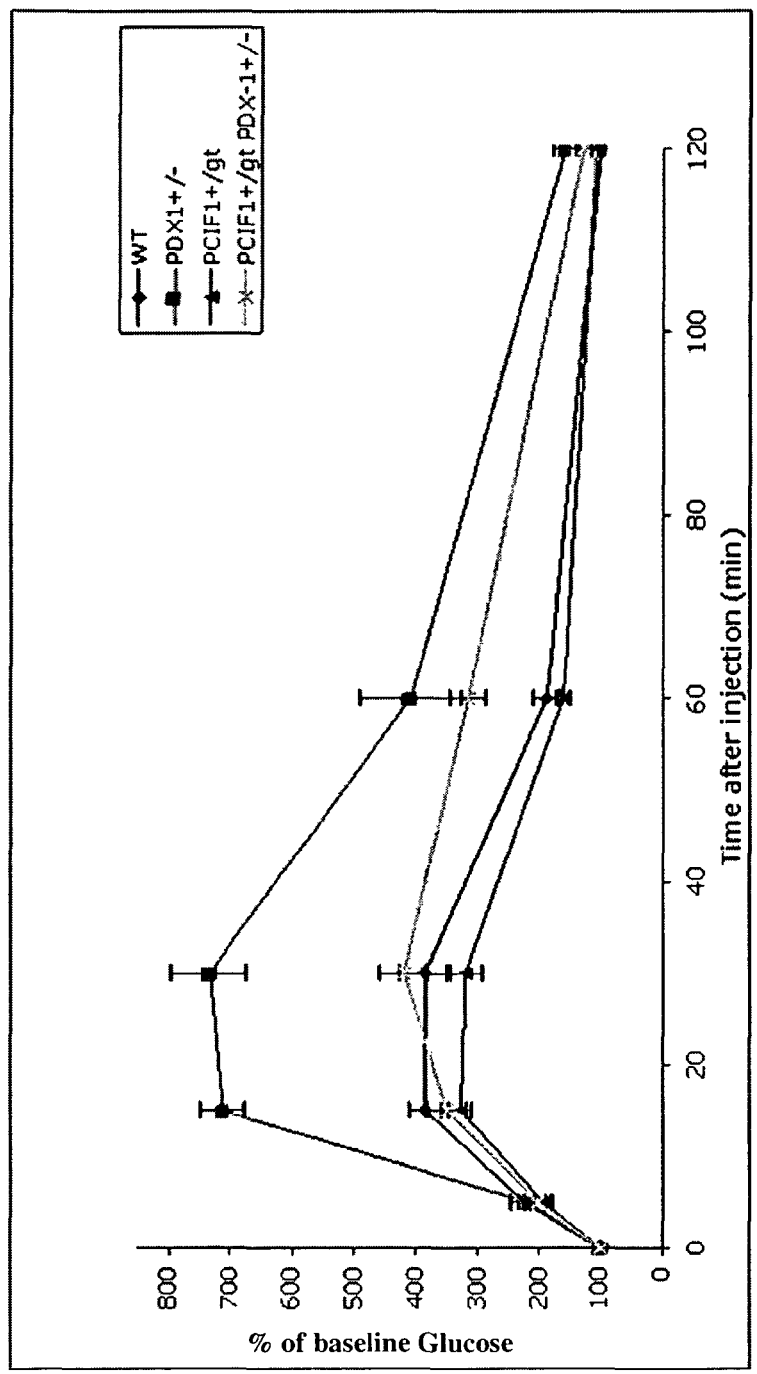
FIG. 13 shows reduction of PCIF1 normalizes glucose tolerance in Pdx1+/− mice.

As shown in FIG. 13, reduction of PCIF1 normalizes glucose tolerance in Pdx1+/– mice: 10-12 week old wild-type, Pdx1+/–, PCIF1 gt/+ and Pdx-1+/– PCIF1 gt/+ females littermates were administered 2 g/kg body weight glucose intraperitoneally, Glucose was measured at 0, 15, 30, 60, 90 and 120 minutes after glucose administration. Statistical significance was determined by ANOVA. Pdx1+/– mice are glucose intolerant, similar to previous reports by several groups. PCIF1 gt/+ mice were similar to wild-type littermates. Strikingly, PCIF1 haploinsufficiency was able to normalize glucose tolerance in Pdx1+/– PCIF1 gt/+ mice. Further, Pdx1+/– mice exhibited a reduction in insulin producing β cell mass, which was normalized by PCIF1 insufficiency (FIG. 16), indicating a genetic interaction between PCIF1 and Pdx1 and consistent with the ability of PCIF1 to negatively regulate Pdx1 activity in cell based assays.

Figure 14:
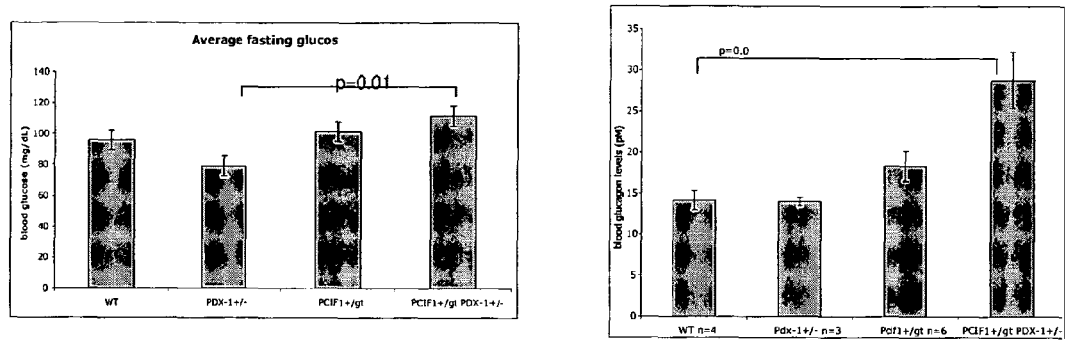
FIG. 14 shows fasting hyperglycemia and hyperglucagonemia in Pdx1+/−PCIF1 gt/+ mice.

As shown in FIG. 14, $Pdx1^{+/-}$ $PCIF1^{gt/+}$ female mice exhibited fasting hyperglycemia and hyperglucagonemia, indicating an additional role for PCIF1 in the development or function of glucagon-producing alpha cells.

Example 11

Over-Expression of PCIF1 and Cullin-3 Promotes Pdx1 Degradation

Figure 15:
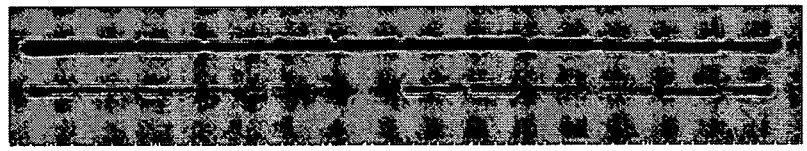
FIG. 15 shows that over-expression of PCIF1 and cullin-3 promotes Pdx1 degradation by the proteasome.
Figure 17:
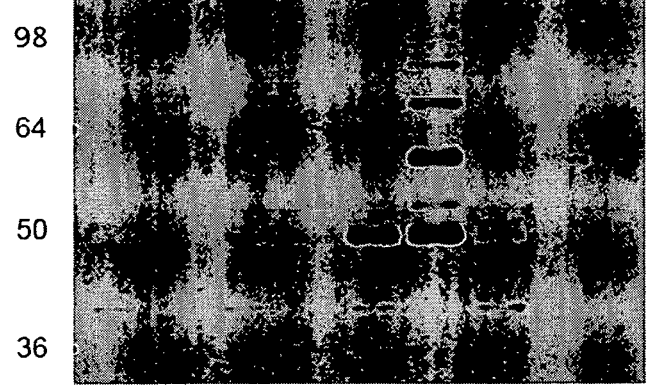
FIG. 17 shows that PCIF1 and Cul3 promote PDX-1 ubiquitination.

Over-expression of PCIF1 and cullin-3 promotes Pdx1 degradation by the proteasome: Expression plasmids for PCIF1, Pdx1 and cullin-3 were transfected into 293T cells and protein extracts were prepared and resolved by SDS-PAGE. As shown in FIG. 15, Pdx1 expression is reduced in the setting of PCIF1/cullin-3 over-expression and this reduction is attenuated by co-administration of MG132, an established proteasome inhibitor. Further, PCIF1 and cullin-3 promote Pdx1 polyubiquitination (FIG. 17). Co-expression of PDX1, PCIF1 and cullin-3 along with myc-tagged Ubiquitin, followed by precipitation with myc-Sepharose and Western blotting for Pdx1 reveals a ladder of polyubiquitinated Pdx1 (lane 6). A mutant form of cullin3 that is not able to interact with the POZ domain does not support Pdx1 polyubiquitination. Taken together, the data indicate that PCIF1 and cullin-3 promote Pdx1 ubquitination, thereby directing Pdx1 for proteasomal degradation.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of increasing pancreatic β-cell mass in a subject, comprising the step of contacting a cell of said subject with a composition comprising: an anti-C-terminal inhibiting factor 1 (anti-PCIF1) antibody capable of inhibiting the binding of C-terminal inhibiting factor 1 (PCIF1) to pancreatic and duodenal homeobox 1 (PDX-1), thereby increasing pancreatic β-cell mass in said subject.

2. A method of increasing glucagon-producing α-cell mass in a subject, comprising the step of contacting a cell of said subject with a composition comprising an anti-C-terminal inhibiting factor 1 (anti-PCIF1) antibody capable of inhibiting the binding of C-terminal inhibiting factor 1 (PCIF1) to pancreatic and duodenal homeobox 1 (PDX-1), thereby increasing glucagon-producing α-cell mass in said subject.

3. A method of treating glucose intolerance in a subject, comprising the step of contacting a cell of said subject with a composition comprising an anti-C-terminal inhibiting factor 1 (anti-PCIF1) antibody capable of inhibiting the binding of C-terminal inhibiting factor 1 (PCIF1) to pancreatic and duodenal homeobox 1 (PDX-1), thereby treating glucose intolerance in said subject.

* * * * *

UNITED STATES PATENT AND TRADEMARK OFFICE
CERTIFICATE OF CORRECTION

PATENT NO. : 9,018,163 B2  
APPLICATION NO. : 12/440900  
DATED : April 28, 2015  
INVENTOR(S) : Doris Stoffers Page 1 of 1

It is certified that error appears in the above-identified patent and that said Letters Patent is hereby corrected as shown below:

Specification

Please replace lines 15-17 in column 1 with the following:

This invention was made with government support under grant number R01 DK068157 and P01 DK049210 awarded by the National Institute of Health. The government has certain rights in the invention.

Signed and Sealed this  
Twelfth Day of April, 2016

Michelle K. Lee  
*Director of the United States Patent and Trademark Office*